(12) United States Patent
Paek (10) Patent No.: US 11,154,857 B2
(45) Date of Patent: Oct. 26, 2021

(54) SINGLE-CHANNEL, HYBRID BIOSENSOR AND SENSOR SYSTEM INCLUDING THE SAME

(71) Applicant: KOREA UNIVERSITY RESEARCH AND BUSINESS FOUNDATION, SEJONG CAMPUS, Sejong-Si (KR)

(72) Inventor: Se-Hwan Paek, Seoul (KR)

(73) Assignee: KOREA UNIVERSITY RESEARCH AND BUSINESS FOUNDATION, SEJONG CAMPUS, Sejong-si (KR)

(*) Notice: Subject to any disclaimer, the term of this patent is extended or adjusted under 35 U.S.C. 154(b) by 219 days.

(21) Appl. No.: 16/389,180

(22) Filed: Apr. 19, 2019

(65) Prior Publication Data
US 2019/0321818 A1 Oct. 24, 2019

(30) Foreign Application Priority Data
Apr. 19, 2018 (KR) .................. 10-2018-0045325

(51) Int. Cl.
*G01N 21/78* (2006.01)
*G01N 33/52* (2006.01)
(Continued)

(52) U.S. Cl.
CPC ............ *B01L 3/5023* (2013.01); *G01N 21/76* (2013.01); *G01N 21/78* (2013.01); *G01N 33/523* (2013.01);
(Continued)

(58) Field of Classification Search
CPC ........... B01L 3/5023; B01L 2400/0406; B01L 2300/0636; B01L 2300/12;
(Continued)

(56) References Cited

U.S. PATENT DOCUMENTS

2004/0214253 A1* 10/2004 Paek .................... G01N 33/558
435/7.92
2007/0015291 A1 1/2007 Smith

FOREIGN PATENT DOCUMENTS

KR 10-2006-0009665 A 2/2006
KR 10-1157042 B1 6/2012

OTHER PUBLICATIONS

Paek, SH, et al. (2017) "Biochemical-Immunological Hybrid Biosensor based on Two-Dimensional Chromatography for On-site Sepsis Diagnosis." Author's Accepted Manuscript, *Biosensors and Bioelectronic*, PII:S0956-5663(17)30405-0, DOI:http://dx.doi.org/10.1016/j.bios.2017.06.032, BOIS9802, pp. 1-25.
(Continued)

*Primary Examiner* — Matthew D Krcha
*Assistant Examiner* — Sophia Y Lyle
(74) *Attorney, Agent, or Firm* — Harness, Dickey & Pierce, P.L.C.

(57) ABSTRACT

A single-channel, chemical-immunological hybrid biosensor is disclosed. According to an embodiment, the hybrid biosensor includes a reaction strip 100 in the form of a porous membrane through which a sample 1 moves by capillary action. the reaction strip 100 is in the form of a porous membrane through which the sample 1 moves by capillary action. Biomarkers in the sample 1 are independently detected based on a chemical reaction and binding reactions on the reaction strip 100.

22 Claims, 6 Drawing Sheets

(51) Int. Cl.
 *B01L 3/00* (2006.01)
 *G01N 33/543* (2006.01)
 *G01N 21/76* (2006.01)
(52) U.S. Cl.
 CPC *G01N 33/54306* (2013.01); *B01L 2300/0636* (2013.01); *B01L 2300/12* (2013.01); *B01L 2400/0406* (2013.01); *G01N 2800/042* (2013.01)
(58) Field of Classification Search
 CPC ....... B01L 2200/025; B01L 2300/0654; G01N 33/523; G01N 33/54306; G01N 21/78; G01N 21/76; G01N 2800/042; G01N 2333/76; G01N 33/723; G01N 2201/0221; G01N 33/558; G01N 33/721; G01N 21/8483; G01N 2333/765
 See application file for complete search history.

(56) References Cited

OTHER PUBLICATIONS

Kouzuma, T., et al. (2004) "Study of glycated amino acid elimination reaction for an improved enzymatic glycated albumin measurement method.", *Clinica Chimica Acta*, 346:135-143.

Higgins, C. (2005) "Hemoglobin and its measurement.", Article downloaded from www.acutecaretesting.org, Jul. 2005, pp. 1-10.

\* cited by examiner

SINGLE-CHANNEL, HYBRID BIOSENSOR AND SENSOR SYSTEM INCLUDING THE SAME

CROSS-REFERENCE TO RELATED APPLICATION

This application claims priority to Korean Patent Application No. 10-2018-0045325 filed on Apr. 19, 2018. The entire disclosure of the application identified in this paragraph is incorporated herein by reference.

FIELD

The present invention relates to a biosensor capable of simultaneously performing a chemical reaction and binding reactions in a single channel or on a single system and a sensor system including the biosensor. More specifically, the present invention relates to a biosensor capable of simultaneously and independently measuring multiple biomarkers detected by different assays based on a chemical reaction and binding reactions in a single fluidic channel in the field of diagnostic testing based on membrane chromatography, and a sensor system including the biosensor.

BACKGROUND

Membrane chromatography offers the advantages of a short turn-around time, simplicity, and practicality compared to conventional in vitro diagnostics in the field of point-of-care-testing (POCT). Particularly, a lateral flow immuno-chromatographic assay (LF-ICA) for which a membrane strip is used is one of the most practical formats and is widely used for POCT due to its ability to detect the presence or absence and the concentration of analytes in a sample within a short time even without using expensive equipment.

In LF-ICA, a nano-sized material, such as colloidal gold, with a large extinction coefficient is employed to produce a color, which can be recognized by the naked eye, and it takes 15 min for all assay processes to complete.

However, inadequate sensitivity of LF-ICA based on gold nanoparticles for the detection of very small amounts of substances in sample (for example, blood sample) needs to be improved for enhanced performance. This need leads to the introduction of sensitive signal generators such as enzymes or fluorescent dyes.

Such conventional immuno-biosensors for POCT are used for the measurement of multiple protein biomarkers as well as single biomarker and exhibit excellent analytical performance with high sensitivity, but fail to acquire information on chemical reaction markers necessary to make a clinical decision regarding particular diseases. For example, the diagnosis of diabetes requires information on the two types of markers, but chemical analyses through chemical reactions cannot be expected in conventional immuno-biosensors for POCT. Thus, the use of separate channels in one system or different assay systems is inevitable for the measurements of heterologous multiple biomarkers.

Consequently, the measurements of heterologous multiple biomarkers detected by different assays through different channels require complex assay systems and different analytical conditions, and such environments deteriorate diagnostic reliability. When blood samples are frequently collected, patients are increasingly subjected to pain, which is likely to be physically stressful, particularly for infants and the elderly, making it impossible to efficiently use limited samples, such as blood samples.

Thus, there is an urgent need for a solution to the problems of conventional immuno-bio sensors.

SUMMARY

The present invention has been made in view of the problems of the prior art, and it is one aspect of the present invention to provide a biosensor that can simultaneously and independently measure heterologous multiple biomarkers, whose detections are dependent on different assays based on a chemical reaction and binding reactions, in a single fluidic channel based on membrane chromatography to diagnose a particular disease.

It is a further aspect of the present invention to provide a sensor system that can measure signals (including chromogenic, luminescent, fluorescent, and electrochemical signals) from a biosensor through suitable signal detectors.

A single-channel, chemical-immunological hybrid biosensor according to an embodiment of the present invention includes a reaction strip in the form of a porous membrane through which a sample moves by capillary action wherein the reaction strip includes: a sample transfer pad having a predetermined length and along which the sample is transferred from one end to the other in the lengthwise direction; one or more immuno-reaction zones including capture recognition elements specifically binding to binding reaction markers in the sample and formed on the sample transfer pad to generate first reaction signals; and at least one chemical reaction zone including a matrix to supply substrate(s) chemically reacting with a chemical reaction marker in the sample to generate a second reaction signal, receiving the sample from the sample transfer pad, spatially separated from the sample transfer pad, and where the chemical reaction occurs independently from the binding reactions.

In the single-channel, chemical-immunological hybrid biosensor, the sample is blood, one of the binding reaction markers is glycated hemoglobin (HbA1c), the chemical reaction marker is total hemoglobin, and the ratio of the concentration of the glycated hemoglobin analyzed as the first reaction signal to the concentration of the total hemoglobin analyzed as the second reaction signal ("% HbA1c") is used to diagnose diabetes.

In the single-channel, chemical-immunological hybrid biosensor, the sample is blood, one of the binding reaction markers is glycated albumin, the chemical reaction marker is total albumin, and the ratio of the concentration of the glycated albumin analyzed as the first reaction signal to the concentration of the total albumin analyzed as the second reaction signal ("% glycated albumin") is used to diagnose diabetes.

In the single-channel, chemical-immunological hybrid biosensor, the matrix includes a signal-generating substrate that directly chemically reacts with the chemical reaction marker to generate the second reaction signal.

In the single-channel, chemical-immunological hybrid biosensor, the sample is blood, the chemical reaction marker is total albumin, and the signal-generating substrate is bromocresol green (BCG) or bromocresol purple (BCP) that generates the second reaction signal suitable as a chromogenic signal for the diagnosis of diabetes.

In the single-channel, chemical-immunological hybrid biosensor, the sample is blood, the chemical reaction marker is total hemoglobin, and the signal-generating substrate is Triton X-100 or sodium lauryl sulphate (SLS) that generates the second reaction signal suitable as a chromogenic signal for the diagnosis of diabetes.

In the single-channel, chemical-immunological hybrid biosensor, the matrix includes a pre-reactive substrate chemically reacting with the chemical reaction marker to produce an intermediate and the signal-generating substrate chemically reacts with the intermediate to generate the second reaction signal.

In the single-channel, chemical-immunological hybrid biosensor, the sample is blood, the chemical reaction marker is total hemoglobin, the pre-reactive substrate is potassium ferricyanide ($K_3Fe(CN)_6$), and the signal-generating substrate is potassium cyanide (KCN) that generates the second reaction signal suitable as a chromogenic signal for the diagnosis of diabetes.

In the single-channel, chemical-immunological hybrid biosensor, the sample is blood, the chemical reaction marker is total hemoglobin, the pre-reactive substrate is sodium nitrite ($NaNO_2$), and the signal-generating substrate is sodium azide ($NaN_3$) that generates the second reaction signal suitable as a chromogenic signal for the diagnosis of diabetes.

In the single-channel, chemical-immunological hybrid biosensor, the sample is blood, the chemical reaction marker is total hemoglobin, the pre-reactive substrate is hydrogen peroxide ($H_2O_2$), and the signal-generating substrate is luminol that generates the second reaction signal suitable as a chromogenic signal for the diagnosis of diabetes.

In the single-channel, chemical-immunological hybrid biosensor, the sample is blood, the chemical reaction marker is total albumin, the pre-reactive substrate includes at least one of methoxy-N-methyl phenazinium methyl sulphate and dithiothreitol, and the signal-generating substrate is 2-(2'-benzothiazolyl)-5-styryl-3-phthalhydrazidyl)-tetrazolium chloride (BSPT) that generates the second reaction signal suitable as a chromogenic signal for the diagnosis of diabetes.

In the single-channel, chemical-immunological hybrid biosensor, the reaction strip further includes at least one chemical reaction pad through which the sample is supplied to the chemical reaction zone; and the chemical reaction zone is arranged on one side of the chemical reaction pad.

In the single-channel, chemical-immunological hybrid biosensor, the number of the immuno-reaction zones is two or more and the capture recognition elements react with the corresponding binding reaction markers in a one-to-one relationship in the immuno-reaction zones.

In the single-channel, chemical-immunological hybrid biosensor, the reaction strip further includes a sample absorption pad arranged at the other end of the sample transfer pad to absorb the sample transferred along the sample transfer pad.

The single-channel, chemical-immunological hybrid biosensor further includes: a sample addition pad absorbing the sample loaded from the outside; and a conjugate pad including detection elements specifically binding to the binding reaction markers in the sample and a signal generator to be conjugated with the detection elements and connecting one end of the sample transfer pad to the sample addition pad, wherein the signal generator produces the first reaction signals when the detection elements, the binding reaction markers, and the capture recognition elements bind together.

In the single-channel, chemical-immunological hybrid biosensor, the conjugate pad is disposed on one end of the sample transfer pad and the sample addition pad is disposed on the conjugate pad.

The single-channel, chemical-immunological hybrid biosensor further includes: a sample addition pad absorbing the sample loaded from the outside and connected to one end of the sample transfer pad; a signal-generating substrate addition pad arranged adjacent to one side of the sample transfer pad and supplying a signal-generating substrate to the sample transfer pad where the signal-generating substrate reacts with binding complexes formed by binding reactions between the binding reaction markers and the capture recognition elements to generate the first reaction signals; and a signal-generating substrate absorption pad adjacent to the other side of the sample transfer pad to absorb the signal-generating substrate transferred across the sample transfer pad.

The single-channel, chemical-immunological hybrid biosensor further includes a cartridge having an accommodation space in which the reaction strip is arranged, a detection window through which the immuno-reaction zones and the chemical reaction zone are exposed, and a sample injection hole through which the sample is loaded into the sample addition pad.

A sensor system according to an embodiment of the present invention includes: the single-channel, chemical-immunological hybrid biosensor; a smart device in which a camera is accommodated to capture chromogenic signals and/or luminescent signals from the single-channel, chemical-immunological hybrid biosensor as an image; and a smart device holder having a slot into which the single-channel, chemical-immunological hybrid biosensor is inserted and adapted to hold the smart device.

The sensor system further includes a light source arranged in the smart device holder to emit light.

The captured signal image is converted into digital data by an application on the smart device.

The sensor system further includes a focusing lens arranged between the camera and at least one of the immuno-reaction zones and the chemical reaction zone to control the focal distance of the camera.

A sensor system according to a further embodiment of the present invention includes the single-channel, chemical-immunological hybrid biosensor and a CMOS image sensor (CIS) capable of capturing chromogenic signals and/or luminescent signals from the single-channel, chemical-immunological hybrid biosensor as an image.

The features and advantages of the present invention will become apparent from the following description with reference to the accompanying drawings.

Prior to the detailed description of the invention, it should be understood that the terms and words used in the specification and the claims are not to be construed as having common and dictionary meanings but are construed as having meanings and concepts corresponding to the technical spirit of the present invention in view of the principle that the inventor can define properly the concept of the terms and words in order to describe his/her invention with the best method.

According to the present invention, the immuno-reaction zones where information on analytical markers through binding reactions is acquired and the chemical reaction zone where information on an analytical marker through a chemical reaction is acquired are independently arranged on the same strip. With this arrangement, the hybrid biosensor of the present invention can simultaneously and independently measure/analyze heterologous multiple biomarkers detected by different assays in a single sample, enabling accurate diagnosis and rapid analysis of a particular disease.

In addition, the sensor system of the present invention is a measurement and analysis system based on a smart device and can be operated for the on-site diagnosis and quantitative analysis of a particular disease in a convenient and economical manner.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION

Other objects, advantages, and novel features of the invention will become more apparent from the following detailed description and preferred embodiments with reference to the appended drawings. In the drawings, the same elements are denoted by the same reference numerals even though they are depicted in different drawings. Although such terms as "first" and "second," etc. may be used to describe various elements, these elements should not be limited by above terms. These terms are used only to distinguish one element from another. In the description of the present invention, detailed explanations of related art are omitted when it is deemed that they may unnecessarily obscure the essence of the present invention.

Preferred embodiments of the present invention will now be described in detail with reference to the accompanying drawings.

Figure 1:
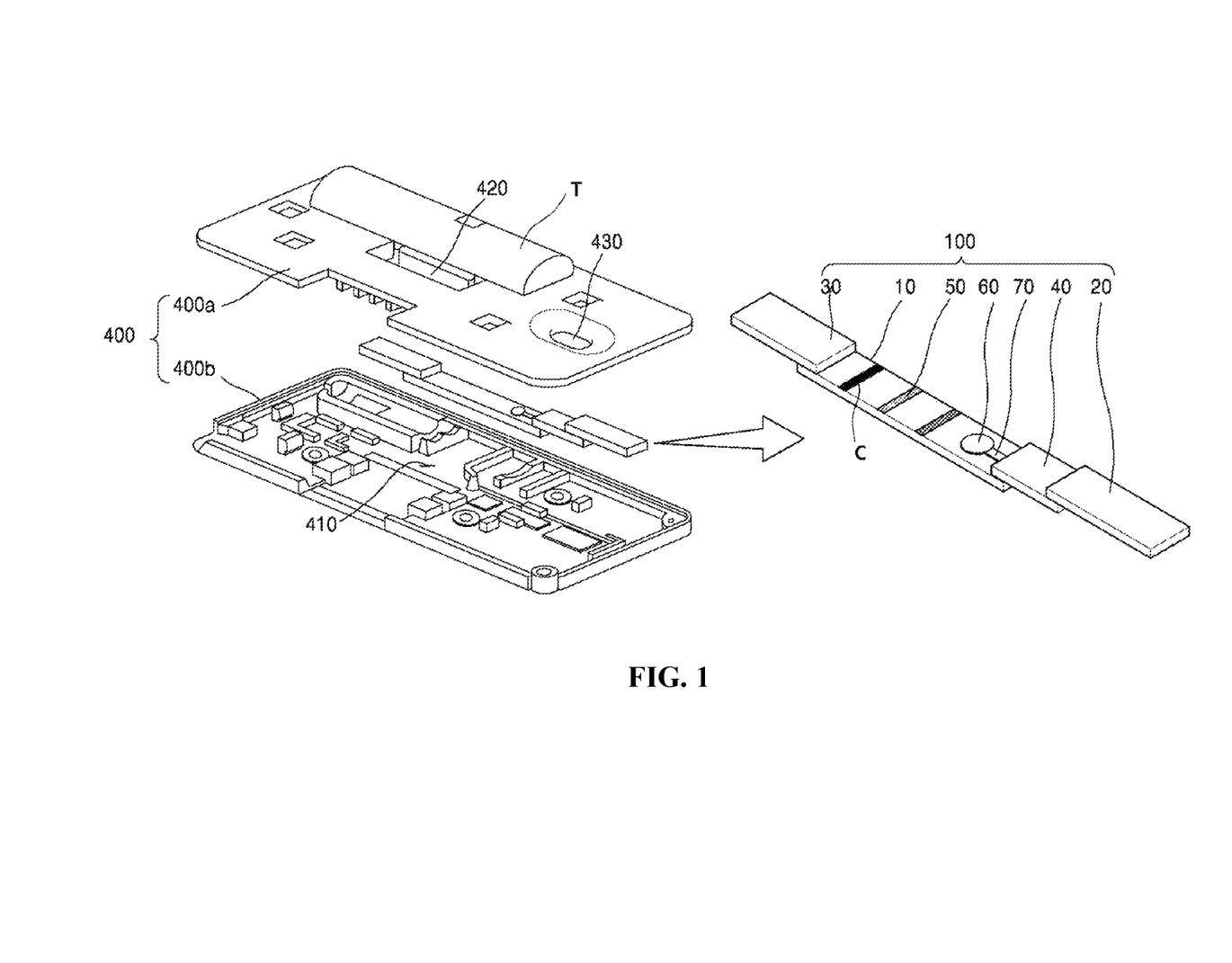
FIG. 1 is an exploded perspective view illustrating a single-channel, chemical-immunological hybrid biosensor according to an embodiment of the present invention.
Figure 2:
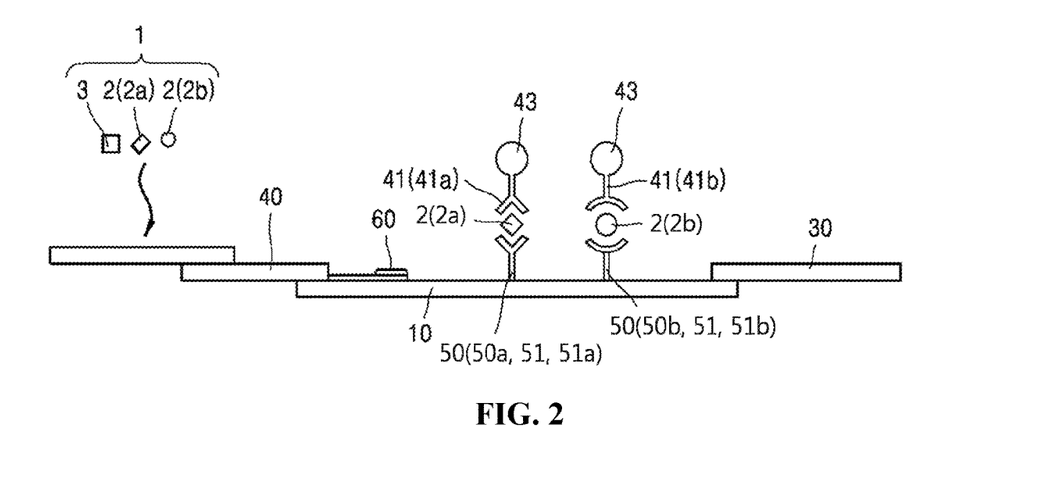
FIG. 2 is a cross-sectional view illustrating the principle of operation of a single-channel, chemical-immunological hybrid biosensor according to an embodiment of the present invention.
Figure 3:
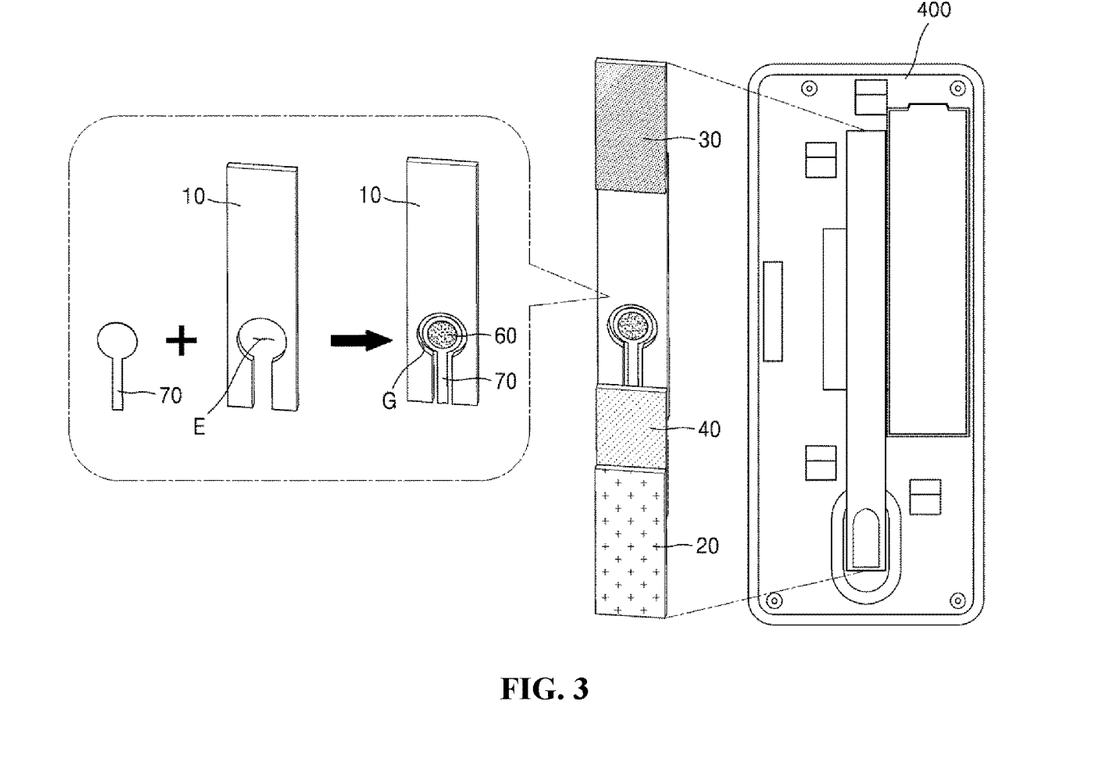
FIG. 3 is a detailed perspective view illustrating a reaction strip of the hybrid biosensor of FIG. 1.

FIG. 1 is an exploded perspective view illustrating a single-channel, chemical-immunological hybrid biosensor according to an embodiment of the present invention, FIG. 2 is a cross-sectional view illustrating the principle of operation of the single-channel, chemical-immunological hybrid biosensor, and FIG. 3 is a detailed perspective view illustrating a reaction strip of the hybrid biosensor.

As illustrated in FIGS. 1 and 2, the single-channel, chemical-immunological hybrid biosensor includes a reaction strip 100 in the form of a porous membrane through which a sample 1 moves by capillary action wherein the reaction strip 100 includes: a sample transfer pad 10 having a predetermined length and along which the sample 1 is transferred from one end to the other in the lengthwise direction; one or more immuno-reaction zones 50 including capture recognition elements 51 specifically binding to binding reaction markers 2 in the sample 1 and formed on the sample transfer pad 10 to generate first reaction signals; and at least one chemical reaction zone 60 including a matrix to supply substrate(s) chemically reacting with a chemical reaction marker 3 in the sample 1 to generate a second reaction signal, receiving the sample 1 from the sample transfer pad 10, spatially separated from the sample transfer pad 10, and where the chemical reaction occurs independently from the binding reactions.

A lateral flow immuno-chromatographic assay (LF-ICA) for which a membrane strip is used is an immunoassay-based medical point-of-care-testing (POCT) technique. Herein, immuno-chromatography refers to a testing method based on a sandwich immunoassay that utilizes specific immuno-reactivity of an antibody against an antigen, color developing properties and flowability of colloidal gold particles, and migration of molecules by capillary action in a membrane. LF-ICA has the ability to detect the presence and concentration of an analyte in a sample within a short time even without using expensive equipment. Due to these advantages, LF-ICA is considered the most practical and is widely used in the POCT field. An immuno-biosensor based on an immuno-chromatographic assay produces a color, which can be recognized by the naked eye, and requires only a very short time for analysis. Furthermore, an immuno-biosensor based on an immuno-chromatographic assay can be used for the measurement of multiple biomarkers as well as single biomarker. However, conventional immuno-biosensors for POCT cannot acquire information on chemical reaction markers necessary to make a clinical decision regarding particular diseases simultaneously with information on immunoassay markers. Thus, the use of separate assay systems is inevitable for the measurements of biomarkers whose analyses are dependent on different assays. The single-channel, chemical-immunological hybrid biosensor for simultaneous measurements of chemical reaction markers and immunoassay markers according to the present invention has been devised in an effort to solve the problems of conventional immuno-biosensors.

Referring to FIG. 3, the reaction strip 100 of the chemical-immunological hybrid biosensor according to the present invention is in the form of a porous membrane through which the sample 1 moves by capillary action. Biomarkers in the sample 1 are independently detected based on a chemical reaction and binding reactions on the reaction strip 100. Biomarkers are indicative of changes in the body. The biomarkers include binding reaction markers 2 and a chemical reaction marker 3. The binding reaction markers 2 can be measured through binding reactions and the chemical reaction marker 3 can be measured through a chemical reaction. The number of the binding reaction markers 2 in the sample is equal to or greater than 2. Therefore, multiple biomarkers can also be detected by the same assay in the reaction strip 100.

The multiple biomarkers detected by different assays in the reaction strip 100 are utilized as data for clinical decision-making for the diagnosis of a particular disease. For example, diabetes is diagnosed by measuring the concentration of glycated hemoglobin (HbA1c) as one of the binding reaction markers 2 in blood and the concentration of total hemoglobin (tHb) as the chemical reaction marker 3 in blood. When hemoglobin in blood is exposed to blood glucose for a long period of time, glucose chemically binds to a specific site on the hemoglobin molecule to produce a chemical species called HbA1c. Here, the ratio of the concentration of glycated hemoglobin (HbA1c) to the concentration of total hemoglobin (tHb) ("% HbA1c") indicates an average blood glucose level after exposure for a long period of time. The % HbA1c value represents an average blood glucose level for about 2-3 months because erythrocytes have a lifetime of about 120 days. This testing method can be used as a measure of blood glucose level management for diabetic patients because it has no limiting or interfering factors.

However, glycated hemoglobin can reflect an average blood glucose level for around 3 months, which corresponds to the lifetime of erythrocytes, but fails to reflect blood glucose level management for a shorter time of several days to several weeks. Further, glycated hemoglobin that mainly reflects the average blood glucose level is not suitable to distinguish patients who suffer from a fluctuation in blood glucose level by repeated hyperglycemia and hypoglycemia. Glycated albumin representing an average blood glucose level during the preceding 1 month can be measured for patients whose blood glucose level management is difficult to accurately perceive with glycated hemoglobin or when further information on blood glucose level management is needed. Accordingly, the ratio of the concentration of glycated albumin (GA) as the binding reaction marker 2 to the concentration of total albumin (tAm) as the chemical reaction marker 3 ("% glycated albumin") can be used as a diagnostic index for diabetes.

Simultaneous analyses of the binding reaction markers 2 and the chemical reaction marker 3 are required for the diagnosis of various diseases, as described above. The single-channel, chemical-immunological hybrid biosensor of the present invention is used mainly for the diagnosis of diabetes but its application is not necessarily limited to diabetic diseases.

Specifically, the reaction strip 100 is constructed to include the sample transfer pad 10, the immuno-reaction zones 50, and the chemical reaction zone 60. This construction enables the detection of heterologous multiple biomarkers in the sample 1 by chemical and immunological assay techniques.

The sample transfer pad 10 has a predetermined length and the sample 1 is transferred from one end to the other end of the sample transfer pad 10 in the lengthwise direction by capillary action. The flow of the sample 1 along the lengthwise direction is defined as a vertical or lengthwise flow. The sample 1 is blood, urine or saliva containing the binding reaction markers 2 and the chemical reaction marker 3. The sample 1 is loaded from the outside and is supplied to the immuno-reaction zones 50 and the chemical reaction zone 60.

The immuno-reaction zones 50 are formed on the sample transfer pad 1. The capture recognition elements 51 are substances that specifically bind to the binding reaction markers 2 through binding reactions. For example, the capture recognition elements 51 may be capture antibodies that specifically bind to the binding reaction markers 2 through antigen-antibody reactions. However, the binding reactions are not necessarily limited to antigen-antibody reactions, and thus the capture recognition elements 51 are not limited to capture antibodies. Other examples of the capture recognition elements 51 include enzymes, receptors, DNA, RNA, PNA, proteins, carbohydrates, minerals, and ions. Any known substances that can specifically bind to each other through physical binding reactions may be used as the binding reaction markers 2 and the capture recognition elements 51.

When the binding reaction markers 2 react with the capture recognition elements 51, first reaction signals are generated from the immuno-reaction zones 50. The intensities of the first reaction signals vary in response to the concentrations of the binding reaction markers 2. Accordingly, the concentrations of the binding reaction markers 2 can be determined from the signals. The first reaction signals are generated by a separate signal generator or signal-generating substrate in a state in which the binding reaction markers 2 react with the capture recognition elements 51. The mechanism of the first reaction signal generation will be described below.

One or more binding reaction markers 2 need to be analyzed for the diagnosis of a particular disease. Thus, two or more immuno-reaction zones 50 are provided. The capture recognition elements may be different substances such that they react with the different binding reaction markers in a one-to-one relationship in the immuno-reaction zones 50. For example, when it is desired to simultaneously analyze glycated hemoglobin 2a and glycated albumin 2b as the binding reaction markers 2 for the diagnosis of diabetes, two immuno-reaction zones 50 are formed. In this case, an anti-glycated hemoglobin capture antibody 51a is present in one of the immuno-reaction zones 50 and an anti-glycated albumin capture antibody 51b is present in the other immuno-reaction zone 50 such that the capture recognition elements 51 bind to the different binding reaction markers 2a and 2b in a one-to-one relationship in the immuno-reaction zones. The glycated hemoglobin 2a and the glycated albumin 2b bind to the different capture antibodies 51a and 51b to generate different first reaction signals from the different immuno-reaction zones 50a and 50b, respectively. Since the first immuno-reaction zone 50a including the anti-glycated hemoglobin capture antibody 51a and the second immuno-reaction zone 50b including the anti-glycated albumin capture antibody 51b are arranged at different positions, the concentrations of the glycated hemoglobin 2a and the glycated albumin 2b can be determined depending on the intensities of the corresponding first reaction signals generated at the positions. However, the anti-glycated hemoglobin capture antibody 51a and the anti-glycated albumin capture antibody 51b do not need to coexist for simultaneous analysis of the glycated hemoglobin 2a and the glycated albumin 2b. Only one of the capture antibodies 51a and 51b may also be provided to selectively analyze the glycated hemoglobin 2a and the glycated albumin 2b.

The chemical reaction zone 60 is provided to analyze the chemical reaction marker 3. The chemical reaction zone 60 includes a matrix to supply substrate(s) that specifically chemically reacts with the chemical reaction marker 3 in the sample 1 to generate a second reaction signal. The chemical reaction between the chemical reaction marker 3 and the substrate enables independent analysis from the above-described binding reactions.

The signal generation from the chemical reaction zone 60 may be induced by one or more reactions depending on its mechanism. The signal generation may be induced by a single reaction. The matrix may include a signal-generating substrate that directly chemically reacts with the chemical reaction marker 3 to generate the second reaction signal. In the case of diabetes diagnosis, Triton X-100 or sodium lauryl sulphate (SLS) may be used as the signal-generating substrate due to its ability to analyze total hemoglobin in blood as the chemical reaction marker 3. Triton X-100 or sodium lauryl sulphate (SLS) chemically reacts with total hemoglobin to generate a chromogenic signal (second reaction signal).

Bromocresol green (BCG) or bromocresol purple (BCP) may be used as the signal-generating substrate for total albumin analysis. Bromocresol green (BCG) or bromocresol purple (BCP) chemically reacts with total albumin to generate a chromogenic signal (second reaction signal).

Alternatively, the signal generation may be induced by a plurality of reactions. In this case, the matrix may include a pre-reactive substrate chemically reacting with the chemical reaction marker 3 to produce an intermediate and a signal-generating substrate chemically reacting with the intermediate to generate the second reaction signal. The pre-reactive substrate primarily chemically reacts with the chemical reaction marker 3 in the sample 1 to produce an intermediate, which secondarily chemically reacts with the signal-generating substrate to generate the second reaction signal.

Specifically, potassium ferricyanide ($K_3Fe(CN)_6$) and potassium cyanide (KCN) can be used as the pre-reactive substrate and the signal-generating substrate, respectively, to quantify total hemoglobin necessary for the diagnosis of diabetes. When the sample 1 reaches the chemical reaction zone 60, potassium ferricyanide oxidizes the iron of heme in the hemoglobin molecule by primary chemical reaction to form methemoglobin (met-Hb) in the ferric state (i.e. iron (III) or $Fe^{3+}$) and the met-Hb is converted to hemiglobincyanide (HiCN) by sequential reaction with KCN to generate a red signal (second reaction signal) in proportion to the hemoglobin concentration. HiCN is a stable colored product and has a maximum wavelength of 540 nm in solution. The intensity of the chromogenic signal is in proportion to the hemoglobin concentration, enabling quantitative analysis of the hemoglobin concentration. Since the concentration of glycated hemoglobin in the corresponding immuno-reaction zone 50 can be quantified, as described above, diabetes can be diagnosed from the ratio of the glycated hemoglobin concentration to the total hemoglobin concentration ("% HbA1c").

As a further example for the diagnosis of diabetes, when the chemical reaction marker 3 is total hemoglobin, sodium nitrite ($NaNO_2$) and sodium azide ($NaN_3$) may be used as the pre-reactive substrate and the signal-generating substrate, respectively. Since the intensity of the chromogenic signal (second reaction signal) is in proportion to the concentration of total hemoglobin, the concentration of total hemoglobin is determined from the signal intensity. Diabetes can be diagnosed from the ratio of the glycated hemoglobin concentration quantified in the corresponding immuno-reaction zone 50 to the total hemoglobin concentration ("% HbA1c").

As another example for the diagnosis of diabetes, total hemoglobin in blood, hydrogen peroxide ($H_2O_2$), and luminol may be used as the chemical reaction marker 3, the pre-reactive substrate, and the signal-generating substrate, respectively. The concentration of total hemoglobin is determined from the intensity of the luminescent signal (second reaction signal). Diabetes can be diagnosed from the ratio of the glycated hemoglobin concentration quantified in the corresponding immuno-reaction zone 50 to the total hemoglobin concentration ("% HbA1c").

Diabetes can also be diagnosed using total albumin as the chemical reaction marker 3. In this case, the pre-reactive substrate may include at least one of methoxy-N-methyl phenazinium methyl sulphate and dithiothreitol, and the signal-generating substrate may be 2-(2'-benzothiazolyl)-5-styryl-3-phthalhydrazidyl)-tetrazolium chloride (BSPT). The intensity of the chromogenic signal (second reaction signal) is in proportion to the concentration of the total albumin, and the concentration of the glycated albumin as the binding reaction marker 2 is quantified by the intensity of the first reaction signal from the corresponding immuno-reaction zone 50. Diabetes can be diagnosed from the ratio of the glycated albumin concentration to the total albumin concentration ("% glycated albumin").

The signal-generating substrate and/or the pre-reactive substrate accumulated in a dry state in the chemical reaction zone 60, are/is dissolved by the sample 1, and react with the chemical reaction marker 3 to generate the second reaction signal.

The chemical reaction in the chemical reaction zone 60 proceeds independently from the binding reactions in the immuno-reaction zones 50. The independent reactions are induced by spatially separating the chemical reaction zone 60 from the sample transfer pad 10 in which the immuno-reaction zones 50 are formed. At least one chemical reaction pad 70 may be used to support the chemical reaction zone 60 and allow the sample 1 to be supplied to the chemical reaction zone 60 therethrough.

The chemical reaction pad 70 is in the form of a porous membrane. The chemical reaction pad 70 is directed toward the other end of the sample transfer pad 10 or is inclined at an angle relative to the lengthwise direction of the sample transfer pad 10. The chemical reaction zone 60 is arranged on one side of the chemical reaction pad 70. The chemical reaction pad 70 may be provided in plurality.

The chemical reaction zone 60 arranged on the chemical reaction pad 70 is spaced apart from the sample transfer pad 10. As an example, the sample transfer pad 10 may be perforated along the thickness direction to form an accommodation portion E in which the chemical reaction pad 70 is arranged, as illustrated in FIG. 3. A gap G is formed between the inner surface of the accommodation portion E and the edge of the chemical reaction pad 70 to prevent contact therebetween such that the sample transfer pad 10 is spatially separated from the chemical reaction zone 60. A sample loading portion is formed at the lower end of the chemical reaction pad 70. The sample loading portion may be connected to a conjugate pad 40 or a sample addition pad 20 to fix the chemical reaction pad 70. Alternatively, only the sample loading portion may be connected to the sample transfer pad 10 through a connection portion and all portions of the chemical reaction pad 70 except the sample loading portion may be separated from the sample transfer pad 10. In this case, although the chemical reaction pad 70 is arranged in the middle of the sample transfer pad 10, a gap is formed between the two pads except the sample loading portion of the chemical reaction pad 70 such that the sample transfer pad 10 is spatially separated from the chemical reaction zone 60 after loading of the sample 1. As a result, the reaction in the chemical reaction zone 60 is allowed to proceed independently without being influenced from vertical and horizontal flows caused by capillary action during analysis of the sample 1. The sample loading portion of the chemical reaction pad 70 provides a passage through which the sample 1 moves to the region of the chemical reaction pad 70 where the chemical reaction zone 60 is arranged.

The accommodation portion E may be formed by etching the sample transfer pad 10 such that it has a shape corresponding to that of the chemical reaction pad 70 and is connected to the chemical reaction pad 70 through the gap G. However, there is no particular restriction on the formation method and shape of the accommodation portion E. The sample transfer pad 10 is not necessarily perforated to form the accommodation portion E so long as the inner surface of the accommodation portion E is spaced apart from the outer surface of the chemical reaction pad 70 over a predetermined area. The accommodation portion E may be concavely depressed from the outer surface of the sample transfer pad 10. The accommodation portion E is not necessarily provided for spatial separation and the chemical reaction pad 70 may be spaced a distance from the outer surface of the sample transfer pad 10.

Since the sample transfer pad 10 formed with the immuno-reaction zones 50 is spatially separated from the chemical reaction zone 60 and/or the chemical reaction pad 70, the sample 1 moving by capillary action is independently subjected to the chemical reaction and immuno-reactions along a single flow to generate first and second chromogenic signals. The sample 1 having undergone the chemical reaction and immuno-reactions is absorbed into a sample absorption pad 30.

The sample absorption pad 30 is arranged on the other end of the sample transfer pad 10. Thus, the sample 1 having undergone the chemical reaction and immuno-reactions is finally absorbed into the sample absorption pad 30. The sample absorption pad 30 may be disposed on the other end of the sample transfer pad 10 but is not necessarily limited to this arrangement.

The reaction strip may further include a sample addition pad 20 absorbing the sample 1 loaded from the outside. The sample addition pad 20 is connected to one end of the sample transfer pad 10. The sample 1 located into the sample addition pad 20 is supplied to the sample transfer pad 10.

The reaction strip may further include a conjugate pad 40 to generate the first reaction signals. The conjugate pad 40 may be in the form of a porous membrane connecting the sample addition pad 20 to one end of the sample transfer pad 10. The conjugate pad 40 is disposed on one end of the sample transfer pad 10 and the sample addition pad 20 is disposed on the conjugate pad 40. However, the scope of the invention is not necessarily limited to this structure. The connection structure may be modified such that the sample 1 can move sequentially through the sample addition pad 20, the conjugate pad 40, and the sample transfer pad 10.

The detection elements 41 and the signal generator 43 are present in the conjugate pad 40. For example, signal generator-detection element conjugates may be accumulated in a dry state in the conjugate pad 40. The detection elements 41 specifically bind to the binding reaction markers 2 in the sample 1 and the signal generator 43 binds to the detection elements 41 to generate first reaction signals in response to the concentrations of the binding reaction markers 2. The first reaction signals are generated only when the detection elements 41, the binding reaction markers 2, and the capture recognition elements 51 bind together to form sandwich (immuno-) complexes. In conclusion, the first reaction signals are generated from the immuno-reaction zones 50.

The signal generator 43 generates the first reaction signals in proportion to the concentrations of the binding reaction markers 2 from the sandwich (immuno-)complexes. The signal generator 43 may be, for example, a colloidal gold particle generating a chromogenic signal, a fluorescent material generating a light signal when excited by a light source or a magnetic material generating a magnetic signal when a magnetic field is applied thereto. The first reaction signals may be, for example, fluorescent, chromogenic, luminescent, electrochemical, thermal and/or magnetic signals depending on the type of the signal generator. A single type of signal generator may be used to generate a single signal or different types of signal generator may be used to generate multiple signals.

Since the conjugates in a dry state are dissolved by the applied sample 1, the detection elements 41 specifically bind to predetermined sites (first sites) of the binding reaction markers 2 in the sample 1, and the binding reaction markers 2 bound to the conjugates move along the sample transfer pad 10 and generate first reaction signals from the immuno-reaction zones 50.

In the previous embodiment, the reaction strip includes the conjugate pad 40 in order to use signal generator-detection element conjugates. However, the use of the conjugate pad 40 is not necessarily required. Hereinafter, a further embodiment based on two-dimensional immuno-chromatography without using the conjugate pad 40 will be described.

Figure 4:
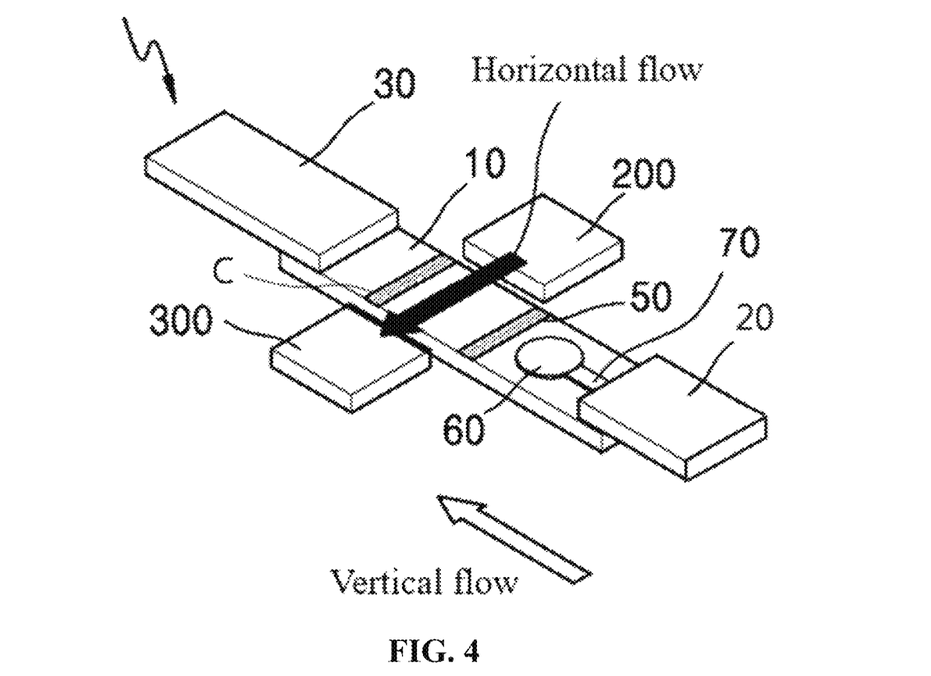
FIG. 4 is a perspective view illustrating a single-channel, chemical-immunological hybrid biosensor according to a further embodiment of the present invention.
Figure 5:
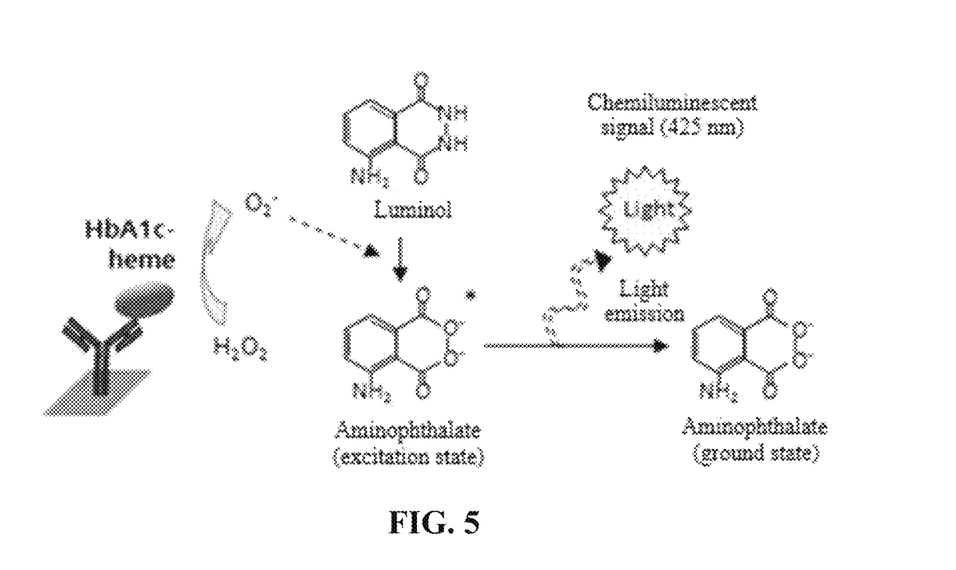
FIG. 5 is a schematic diagram showing the mechanism of chemiluminescent signal generation via a catalytic reaction of heme in the hemoglobin molecule when luminol as a luminescent substrate was added for hemoglobin detection.

FIG. 4 is a perspective view illustrating a single-channel, chemical-immunological hybrid biosensor according to a further embodiment of the present invention and FIG. 5 is a schematic diagram showing the mechanism of chemiluminescent signal generation via a catalytic reaction of heme in the hemoglobin molecule when luminol as a luminescent substrate was added for hemoglobin detection.

The single-channel, chemical-immunological hybrid biosensor may further include a signal-generating substrate addition pad 200 and a signal-generating substrate absorption pad 300. The signal-generating substrate addition pad 200 is in the form of a porous membrane that absorbs a substrate loaded from the outside. The signal-generating substrate addition pad 200 is arranged adjacent to one side of the sample transfer pad 10. The signal-generating substrate flows along the widthwise direction of the sample transfer pad 10 ("horizontal flow") and reacts with reaction complexes formed by the binding reactions between the binding reaction markers and the capture recognition elements in the immuno-reaction zones 50 to generate first reaction signals.

The signal-generating substrate absorption pad 300 is disposed adjacent to the other side of the sample transfer pad 10. That is, the signal-generating substrate absorption pad 300 is arranged to face the signal-generating substrate addition pad 200 through the sample transfer pad 10. With this arrangement, the signal-generating substrate is absorbed into the signal-generating substrate absorption pad 300 across the sample transfer pad 10

The biosensor of the previous embodiment uses typical immunoassay formats based on the formation of sandwich immuno-complexes from capture antibodies (capture recognition elements) and detection antibodies (detection elements) for the immunoassay of HbA1c, as in conventional assays. In this case, detection antibodies labeled with signal generators such as gold particles should be used to generate signals from analyte-capture antibody complexes after sample loading. In contrast, the immunoassay of hemoglobin does not necessarily require the use of detection elements conjugated with a signal generator. This is because iron-containing heme in the HbA1c molecule acts as a catalyst for the redox reaction of hydrogen peroxide ($H_2O_2$). Heme is a complex containing one iron atom in a porphyrin structure and is well known as a component of hemoglobin that makes blood look red. Referring to FIG. 5, the use of luminol as the signal-generating substrate based on such characteristics of hemoglobin enables the analysis of hemoglobin. This is based on the catalysis of iron present in hemoglobin, as described above. Luminol can also be used to detect copper, iron, and cyanides in biological analysis.

These target materials can be identified through the generation of blue light from luminol in the dark after addition of a luminol signal-generating substrate solution. Accordingly, when a blood sample is loaded into the sample addition pad 20, glycated hemoglobin in the sample moves along the sample transfer pad 10 and reacts with the capture antibody (capture recognition element) in the immuno-reaction zone 50 to form immuno-complexes. Then, luminol as the signal-generating substrate is supplied through the signal-generating substrate addition pad 200 and flows along the horizontal flow. Luminescent signals are generated from the immuno-reaction zone 50 for HbA1c measurement through catalytic reactions.

To generate a constant control signal irrespective of the concentration of analyte, an anti-hemoglobin antibody can be immobilized onto a control site C on the top end of the immuno-reaction zone 50. In this case, total hemoglobin is present at a very higher concentration in the sample compared to glycated hemoglobin, thus being suitable for generating a constant control signal. However, it is very difficult for this immunoassay to obtain a high resolution signal in proportion to the concentration of total hemoglobin without additional dilution of the sample.

The chemical reaction pad 70 is arranged such that an empty space (i.e., gap G), is formed between the chemical reaction pad 70 and the sample transfer pad 10, as described above with reference to FIG. 3. With this arrangement, the chemical reaction is not affected by the horizontal flow. Here, the empty space formed along the edge of the chemical reaction pad 70 acts as a barrier to capillary action to prevent the horizontal flow of the signal-generating substrate from entering the chemical reaction zone 60.

Taken together, the single-channel, chemical-immunological hybrid biosensor of the present invention has a structure in which the immuno-reaction zones 50 where information on the binding reaction markers is acquired through the antigen-antibody reactions and the chemical reaction zone 60 where information on the chemical reaction marker 3 is acquired through the chemical reaction are arranged on the same strip. This structure enables the diagnosis of a disease from a single sample (e.g., blood) so that patient's pain, which is likely to be stressful, can be alleviated and allows for efficient use of the limited sample. In addition, the single-channel, chemical-immunological hybrid biosensor of the present invention can simultaneously measure/analyze heterologous multiple biomarkers in a single sample in an independent manner, enabling accurate diagnosis and rapid analysis of a disease. Furthermore, the single-channel, chemical-immunological hybrid biosensor of the present invention does not require time to render a separate analyzer ready for operation so that the sample (e.g., blood) can be prevented from being contaminated. Moreover, the single-channel, chemical-immunological hybrid biosensor of the present invention can simultaneously measure disease-related multiple biomarkers in several patients in urgent situations, for example, in emergency rooms of hospitals, and can analyze without imposing an economic burden on people from developing countries and ordinary people with low levels of income.

Figure 6:
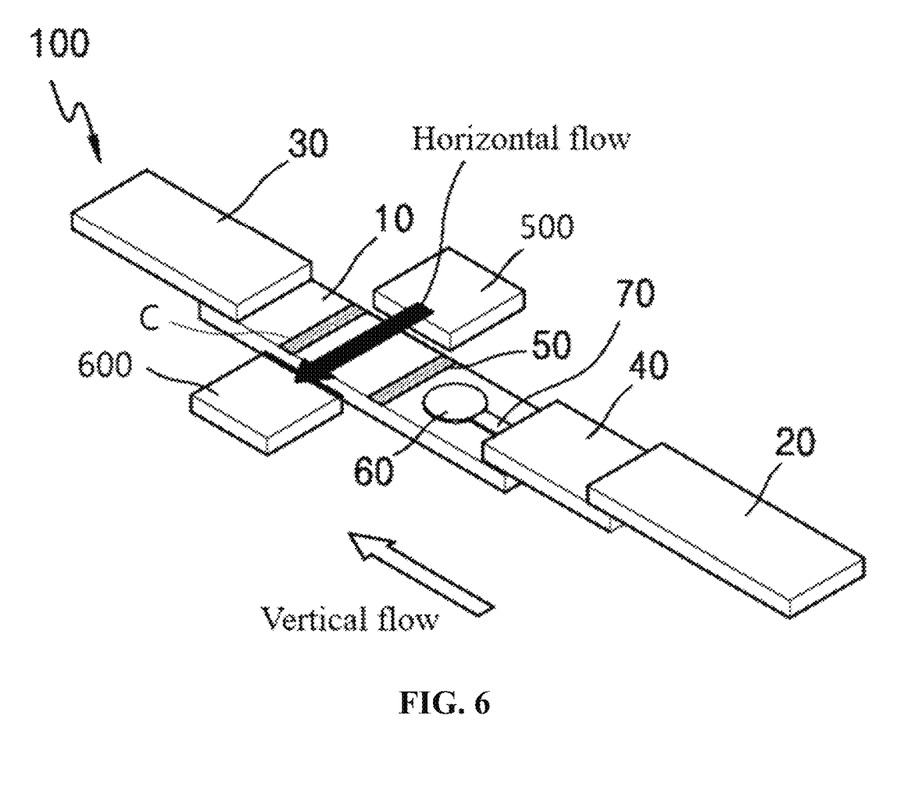
FIG. 6 is a perspective view illustrating a single-channel, chemical-immunological hybrid biosensor according to another embodiment of the present invention.

FIG. 6 is a perspective view illustrating a single-channel, chemical-immunological hybrid biosensor according to another embodiment of the present invention.

As illustrated in FIG. 6, the single-channel, chemical-immunological hybrid biosensor includes a reaction strip in which a conjugate pad 40 is arranged. The hybrid biosensor needs to be washed after the binding reactions. The washing is performed in a simple manner by a two-dimensional immuno-chromatographic assay. To this end, the single-channel, chemical-immunological hybrid biosensor may further include a substrate addition pad 500 and a substrate absorption pad 600. The substrate addition pad 500 is in the form of a porous membrane that absorbs a substrate loaded from the outside. The substrate addition pad 500 is arranged adjacent to one side of the sample transfer pad 10. The substrate absorption pad 600 is arranged at the other side of the sample transfer pad 10. With this arrangement, the substrate moves across the sample transfer pad 10 from the substrate addition pad 500, that is, in the widthwise direction of the sample transfer pad 10, and is absorbed into the substrate absorption pad 600. The movement of the substrate is defined as a "horizontal or widthwise flow").

Referring to FIG. 1, the single-channel, chemical-immunological hybrid biosensor of the present invention may further include a cartridge 400 accommodating the reaction strip 100. The conjugate pad 40 is provided in the reaction strip 100, as illustrated in FIG. 1. Alternatively, the conjugate pad 40 may be omitted (see FIG. 4). The cartridge 400 has an internal accommodation space 410 in which the reaction strip 100 is accommodated. The cartridge 400 is perforated to form a sample injection hole 430 through which the accommodation space 410 is in communication with the outside and the sample 1 is introduced into the reaction strip 100. The cartridge 400 is also perforated to provide detection window 420 through which the immuno-reaction zones 50 and the chemical reaction zone 60 are exposed. Chromogenic signals from the reaction zones 50 and 60 can be observed from the outside through the detection window. As described above, the signal-generating substrate addition pad 200, the signal-generating substrate absorption pad 300, the substrate addition pad 500, and the substrate absorption pad 600 may be arranged in the cartridge 400. A substrate injection hole through which the (signal-generating) substrate can be injected into the (signal-generating) substrate addition pad may be formed in the cartridge 400. The cartridge 400 may include a substrate accommodating tank T.

The cartridge 400 consists of a top plate 400a and a bottom plate 400b between which the reaction strip 100 is arranged. The top plate 400a can be coupled to the bottom plate 400b to fix the reaction strip 100 in the cartridge 400. However, the cartridge 400 may not necessarily consist of the top plate 400a and the bottom plate 400b. For example, the cartridge 400 may be produced in one piece in which the reaction strip 100 is inserted. Since the substrate absorption pad 600 is exchanged during 2-dimensional immuno-chromatographic assay, the cartridge 400 is designed such that the substrate absorption pad 600 is easily detachable from the place where it is located.

The biomarkers detected by the single-channel, chemical-immunological hybrid biosensor of the present invention can be quantitatively analyzed simultaneously with on-site detection by a signal detection system, which will be explained below.

Figure 7:
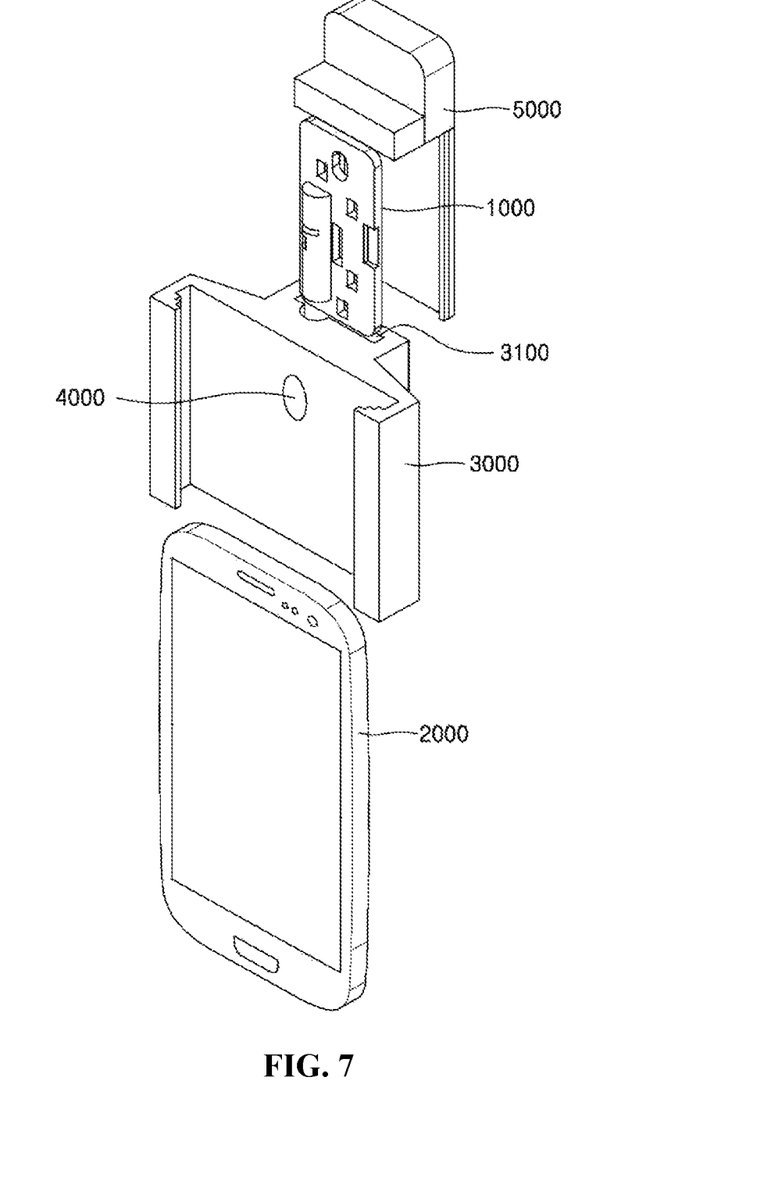
FIG. 7 is a perspective view illustrating a sensor system including according to an embodiment of the present invention.

FIG. 7 is a perspective view illustrating a sensor system according to an embodiment of the present invention.

As illustrated in FIG. 7, the sensor system includes: the single-channel, chemical-immunological hybrid biosensor 1000; a smart device 2000 in which a camera is accommodated to capture chromogenic signals and/or luminescent signals from the single-channel, chemical-immunological hybrid biosensor as an image; and a smart device holder 3000 having a slot 3100 into which the single-channel, chemical-immunological hybrid biosensor 1000 is inserted and adapted to hold the smart device 2000.

The single-channel, chemical-immunological hybrid biosensor 1000 is the same as that described above and a detailed description thereof is thus omitted.

The smart device 2000 refers to a device, such as a smartphone, a tablet computer, or a notebook computer, whose function is not limited and can be altered or extended to a considerable extent through an application program, such as a mobile application. The lens of the camera accommodated in the smart device 2000 is arranged to face the immuno-reaction zones 50 and/or the chemical reaction zone 60. With this arrangement, the camera can capture the chromogenic signals and/or luminescent signals as an image.

The smart device 2000 and the single-channel, chemical-immunological hybrid biosensor 1000 are held by the smart device holder 3000. The smart device holder 3000 has a stand holding the smart device 2000 and a slot 3100 into which the single-channel, chemical-immunological hybrid biosensor 1000 is inserted. The single-channel, chemical-immunological hybrid biosensor 1000 inserted into the slot 310 may be fixed by a cover 5000.

The sensor system of the present invention may further include a focusing lens 4000. The focusing lens 4000 is adapted to control the focal distance of the camera. The focusing lens 4000 can be arranged between the camera and the immuno-reaction zone 50 and/or the chemical reaction zone 60 to improve the resolution of the luminescent and/or chromogenic signal image.

The sensor system of the present invention further includes a light source arranged in the smart device holder 3000. The light source may be, for example, an LED lamp. The light source can be automatically turned on when the smart device 2000 is held by the stand. The single-channel, chemical-immunological hybrid biosensor 1000 generating chromogenic signals by a chemical reaction and immuno-reactions is inserted into the slot 3100 and the camera can capture the chromogenic signals generated from the single-channel, chemical-immunological hybrid biosensor 1000 as an image.

The captured image is converted into digital data, which can be utilized as information for quantitative analysis. The conversion into digital data can be accomplished by a suitable application on the smart device 2000.

On the other hand, the biomarkers detected by the single-channel, chemical-immunological hybrid biosensor of the present invention can be quantitatively analyzed by a signal detection system based on an independent specialized device, which will be described below.

Figure 8:
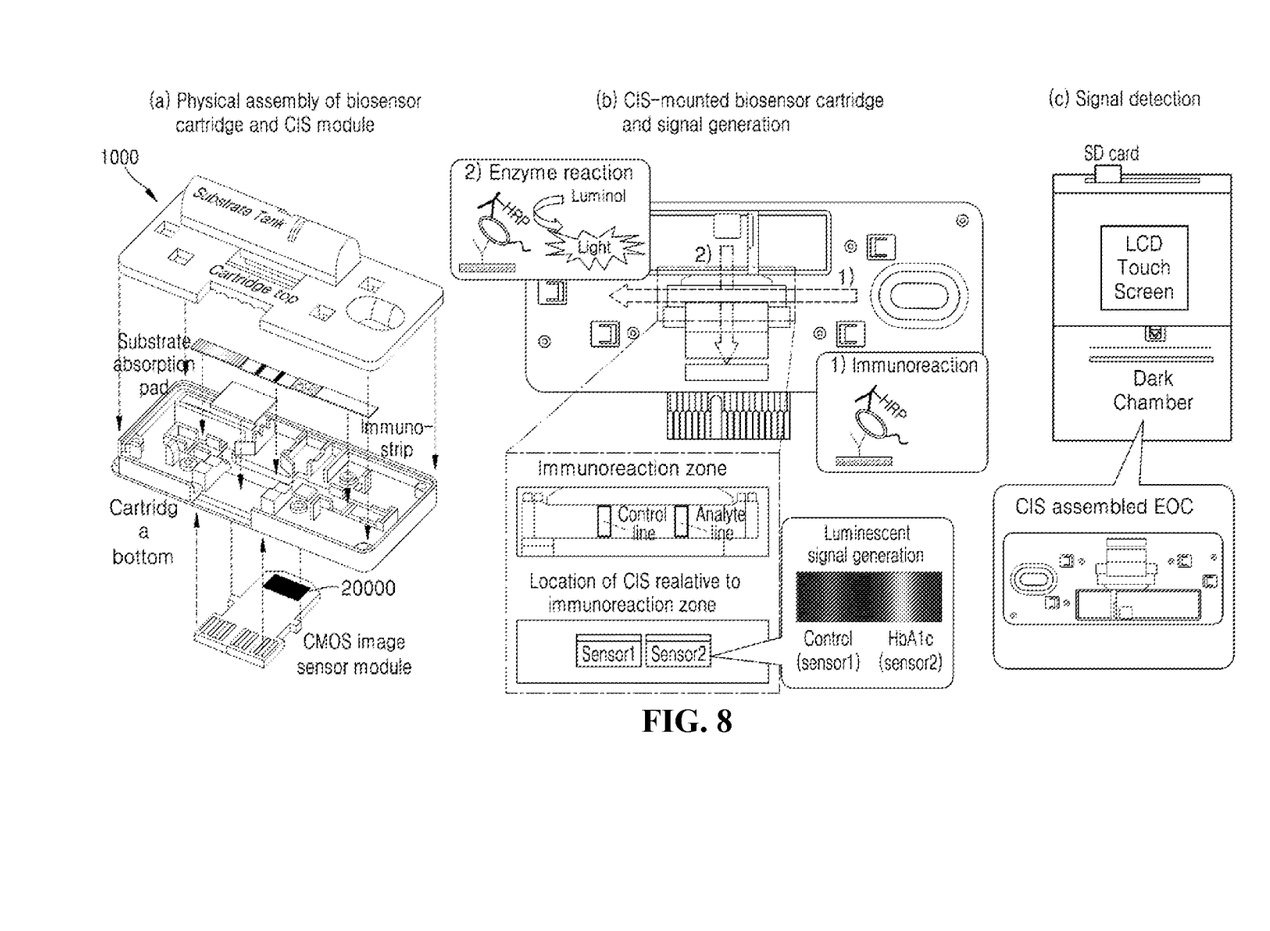
FIG. 8 illustrates a sensor system according to a further embodiment of the present invention.

FIG. 8 illustrates a sensor system according to a further embodiment of the present invention.

The sensor system of this embodiment includes the single-channel, chemical-immunological hybrid biosensor 1000 and a CMOS image sensor (CIS) 20000 capable of capturing chromogenic signals and/or luminescent signals from the single-channel, chemical-immunological hybrid biosensor as an image.

The sensor system proposed in this embodiment is a type of device for quantitative analysis of signal in which a complementary metal-oxide-semiconductor (CMOS) image sensor (CIS) module is coupled to the cartridge of the biosensor 1000.

As described above, the generation of chemiluminescent signals from the hemoglobin molecule captured by antigen-antibody reactions in the reaction strip is attributed to the oxidation of luminol via a catalytic reaction of iron atoms in the heme structure in the presence of hydrogen peroxide (oxidant) in the substrate solution. As a result of the reaction, a denitrified, unstable organic peroxide is formed and such excited state of the component is then converted to the ground state by rearranging electrons to emit energy in the form of photons, which corresponds to blue light at a wavelength of 425 nm.

An image sensor can be used for light detection. Image sensors refer to devices that sense the intensity and color of light, and convert the detected signals into digital image data. Image sensors can be divided into charge-coupled devices (CCD) and CMOS image sensors according to the conversion mode.

Although not illustrated in FIG. 8, the cooled-charge-coupled device (CCD) is installed in a dark chamber to capture chemiluminescent images from the cartridge. The luminescent signals from the cartridge of the biosensor reach a maximum intensity within 30 seconds after addition of the luminol substrate solution, and thereafter, the signal intensity decreases gradually because the substrate is consumed rapidly, limiting its diffusion.

The CMOS image sensor 20000 is used to make the biosensor system portable for convenient use in POCT. The lens-free semiconductor (CMOS) image sensor (CIS) 20000 may be introduced for the measurement of luminescent signals. Two CISs 20000 may be mounted on a printed circuit board (PCB) to fabricate a CIS module (see (a) of FIG. 8). The CISs 20000 are located physically close to the HbA1c analysis line and the control line of the sample transfer pad of the reaction strip, where light signals are generated, in a one-to-one relationship to measure the light signals (see (a) and (b) of FIG. 8).

The CISs 20000 adjacent to sites where light signals are generated allow for efficient photon transfer. The use of the lens-free CIS 20000 can save the space necessary for the focal distance of the camera, achieving miniaturization of the sensor system. The CIS module is mounted in the cartridge of the single-channel, chemical-immunological hybrid biosensor 10000. The sensor system is arranged in a dark chamber to capture chemiluminescent images (see (c) of FIG. 8).

Further, the lens-free CIS 20000 can be used to fabricate a color detector. As mentioned in the smartphone-based color detector, signal images can be captured by the camera accommodated in the smartphone as a combination of the image sensor and the lens only when the focal distance is maintained at a constant level. Likewise, color images can be captured with the lens-free CIS 20000 under illumination. In this case, since the CIS 20000 should be in close contact with a subject, signals can be read through a translucent NC membrane constituting the sample transfer pad when light is irradiated from the opposite direction. This process can be controlled using the smartphone via the Bluetooth connection, as in the smartphone-based detector, and the signals can be processed and transmitted over the world wide web and through the Wi-Fi network.

Therefore, the use of the lens-free CIS 20000 enables analysis control, signal detection, and web transmission in an independent manner without any change in the design of the detector irrespective of the model of the smartphone, making the system more compact and portable.

Overall, the sensor system of the present invention is a measurement and analysis system based on a smart device and can be operated for the on-site diagnosis and quantitative analysis of a particular disease in a convenient and economical manner. In addition, the use of the lens-free CIS is advantageous in fabricating chromogenic signal and luminescent signal detectors.

Although the present invention has been described herein with reference to the specific embodiments, these embodiments do not serve to limit the invention and are set forth for illustrative purposes. It will be apparent to those skilled in the art that modifications and improvements can be made without departing from the spirit and scope of the invention.

Such simple modifications and improvements of the present invention belong to the scope of the present invention, and the specific scope of the present invention will be clearly defined by the appended claims.

What is claimed is:

1. A single-channel, chemical-immunological hybrid biosensor comprising a reaction strip in the form of a porous membrane through which a sample moves by capillary action wherein the reaction strip comprises: a sample transfer pad having a predetermined length and along which the sample is transferred from one end to the other in the lengthwise direction; one or more immuno-reaction zones comprising capture recognition elements specifically binding to binding reaction markers in the sample to generate first reaction signals on the sample transfer pad; at least one chemical reaction zone comprising a matrix to supply substrate(s) chemically reacting with a chemical reaction marker in the sample to generate a second reaction signal, where the sample is received in a manner that is spatially separated from the sample transfer pad and, thus, the chemical reaction occurs independently from the binding reactions; a sample addition pad absorbing the sample loaded from the outside and connected to one end of the sample transfer pad; a signal-generating substrate addition pad arranged adjacent to one side of the sample transfer pad and supplying a signal-generating substrate to the sample transfer pad where the signal-generating substrate reacts with reaction complexes formed by binding reactions between the binding reaction markers and the capture recognition elements to generate the first reaction signals; and a signal-generating substrate absorption pad adjacent to the other side of the sample transfer pad to absorb the signal-generating substrate transferred across the sample transfer pad.

2. The single-channel, chemical-immunological hybrid biosensor according to claim 1, wherein the sample is blood, one of the binding reaction markers is glycated hemoglobin (HbA1c), the chemical reaction marker is total hemoglobin, and the ratio of the concentration of the glycated hemoglobin analyzed as the first reaction signal to the concentration of the total hemoglobin analyzed as the second reaction signal ("% HbA1c") is used to diagnose diabetes.

3. The single-channel, chemical-immunological hybrid biosensor according to claim 1, wherein the sample is blood, one of the binding reaction markers is glycated albumin, the chemical reaction marker is total albumin, and the ratio of the concentration of the glycated albumin analyzed as the first reaction signal to the concentration of the total albumin analyzed as the second reaction signal ("% glycated albumin") is used to diagnose diabetes.

4. The single-channel, chemical-immunological hybrid biosensor according to claim 1, wherein the matrix comprises a signal-generating substrate that directly chemically reacts with the chemical reaction marker to generate the second reaction signal.

5. The single-channel, chemical-immunological hybrid biosensor according to claim 4, wherein the sample is blood, the chemical reaction marker is total albumin, and the signal-generating substrate is bromocresol green (BCG) or bromocresol purple (BCP) that generates the second reaction signal suitable as a chromogenic signal for the diagnosis of diabetes.

6. The single-channel, chemical-immunological hybrid biosensor according to claim 4, wherein the sample is blood, the chemical reaction marker is total hemoglobin, and the signal-generating substrate is 2-[4-(2,4,4-trimethylpentan-2-yl)phenoxy]ethanol (octyl phenol ethoxylate) sodium lauryl sulphate (SLS) that generates the second reaction signal suitable as a chromogenic signal for the diagnosis of diabetes.

7. The single-channel, chemical-immunological hybrid biosensor according to claim 4, wherein the matrix comprises a pre-reactive substrate chemically reacting with the chemical reaction marker to produce an intermediate and the signal-generating substrate chemically reacts with the intermediate to generate the second reaction signal.

8. The single-channel, chemical-immunological hybrid biosensor according to claim 7, wherein the sample is blood, the chemical reaction marker is total hemoglobin, the pre-reactive substrate is potassium ferricyanide ($K_3Fe(CN)_6$), and the signal-generating substrate is potassium cyanide (KCN) that generates the second reaction signal suitable as a chromogenic signal for the diagnosis of diabetes.

9. The single-channel, chemical-immunological hybrid biosensor according to claim 7, wherein the sample is blood, the chemical reaction marker is total hemoglobin, the pre-reactive substrate is sodium nitrite ($NaNO_2$), and the signal-generating substrate is sodium azide ($NaN_3$) that generates the second reaction signal suitable as a chromogenic signal for the diagnosis of diabetes.

10. The single-channel, chemical-immunological hybrid biosensor according to claim 7, wherein the sample is blood, the chemical reaction marker is total hemoglobin, the pre-reactive substrate is hydrogen peroxide ($H_2O_2$), and the signal-generating substrate is luminol that generates the second reaction signal suitable as a chromogenic signal for the diagnosis of diabetes.

11. The single-channel, chemical-immunological hybrid biosensor according to claim 7, wherein the sample is blood, the chemical reaction marker is total albumin, the pre-reactive substrate comprises at least one of methoxy-N-methyl *phenazinium* methyl sulphate and dithiothreitol, and the signal-generating substrate is 2-(2'-benzothiazolyl)-5-styryl-3-phthalhydrazidyl)-tetrazolium chloride (BSPT) that generates the second reaction signal suitable as a chromogenic signal for the diagnosis of diabetes.

12. The single-channel, chemical-immunological hybrid biosensor according to claim 1, wherein the reaction strip further comprises at least one chemical reaction pad through which the sample is supplied to the at least one chemical reaction zone; and the at least one chemical reaction zone is arranged on one side of the chemical reaction pad.

13. The single-channel, chemical-immunological hybrid biosensor according to claim 1, wherein the number of the immuno-reaction zones is two or more and the capture recognition elements react with the corresponding binding reaction markers in a one-to-one relationship in the immuno-reaction zones.

14. The single-channel, chemical-immunological hybrid biosensor according to claim 1, wherein the reaction strip further comprises a sample absorption pad arranged at the other end of the sample transfer pad to absorb the sample transferred along the sample transfer pad.

15. The single-channel, chemical-immunological hybrid biosensor according to claim 1, further comprising a sample addition pad absorbing the sample loaded from the outside; and a conjugate pad comprising detection elements specifically binding to the binding reaction markers in the sample and a signal generator to be conjugated with the detection elements, and connecting one end of the sample transfer pad to the sample addition pad, wherein the signal generator generates the first reaction signals when the detection elements, the binding reaction markers, and the capture recognition elements bind together.

16. The single-channel, chemical-immunological hybrid biosensor according to claim 15, wherein the conjugate pad is disposed on one end of the sample transfer pad and the sample addition pad is disposed on the conjugate pad.

17. The single-channel, chemical-immunological hybrid biosensor according to claim 1, further comprising a cartridge having an accommodation space in which the reaction strip is arranged, a detection window through which the immuno-reaction zones and the at least one chemical reaction zone are exposed, and a sample injection hole through which the sample is loaded into the sample addition pad.

18. A sensor system comprising: the single-channel, chemical-immunological hybrid biosensor according to claim 1, a smart device in which a camera is accommodated to capture chromogenic signals and/or luminescent signals from the single-channel, chemical-immunological hybrid biosensor as an image; and a smart device holder having a slot into which the single-channel, chemical-immunological hybrid biosensor is inserted and adapted to hold the smart device.

19. The sensor system according to claim 18, further comprising a light source arranged in the smart device holder to emit light.

20. The sensor system according to claim 18, wherein the captured signal image is converted into digital data by an application on the smart device.

21. The sensor system according to claim 18, further comprising a focusing lens arranged between the camera and at least one of the immuno-reaction zones and the at least one chemical reaction zone to control the focal distance of the camera.

22. A sensor system comprising the single-channel, chemical-immunological hybrid biosensor according to claim 1 and a CMOS image sensor (CIS) capable of capturing chromogenic signals and/or luminescent signals from the single-channel, chemical-immunological hybrid biosensor as an image.

* * * * *